(12) United States Patent
Stefanski (10) Patent No.: US 10,064,999 B2
(45) Date of Patent: Sep. 4, 2018

(54) AUTOMATIC APPLICATOR FOR LIQUID PHARMACEUTICAL PREPARATIONS, PARTICULARLY FOR INSULIN

(71) Applicant: COPERNICUS Sp. Z o.o., Szczecin (PL)

(72) Inventor: Adam Stefanski, Gniezno (PL)

(73) Assignee: COPERNICUS SP. Z O.O., Szczecin (PL)

( * ) Notice: Subject to any disclaimer, the term of this patent is extended or adjusted under 35 U.S.C. 154(b) by 0 days.

(21) Appl. No.: 15/869,632

(22) Filed: Jan. 12, 2018

(65) Prior Publication Data

US 2018/0133406 A1    May 17, 2018

Related U.S. Application Data

(63) Continuation of application No. 15/388,385, filed on Dec. 22, 2016, now Pat. No. 9,895,495, which is a (Continued)

(51) Int. Cl.
*A61M 5/315* (2006.01)
*A61M 5/20* (2006.01)
(Continued)

(52) U.S. Cl.
CPC .......... *A61M 5/31543* (2013.01); *A61M 5/20* (2013.01); *A61M 5/24* (2013.01);
(Continued)

(58) Field of Classification Search
CPC .. A61M 5/24; A61M 5/3155; A61M 5/31551; A61M 5/31553; A61M 5/31555; A61M 2005/3115; A61M 2005/202
See application file for complete search history.

(56) References Cited

U.S. PATENT DOCUMENTS 4,883,472 A    11/1989  Michel
5,104,380 A     4/1992  Holman et al.
(Continued)

FOREIGN PATENT DOCUMENTS

CN    1277558 A    12/2000
CN    1509193 A     6/2004
(Continued)

*Primary Examiner* — Nathan R Price
*Assistant Examiner* — Anh Bui
(74) *Attorney, Agent, or Firm* — Buchanan Ingersoll & Rooney PC (57) ABSTRACT

An automatic applicator for liquid pharmaceutical preparations, particularly for multiple injection application of set doses of a medicine from an exchangeable container is provided. The automatic applicator includes a body housing connected to a housing of an exchangeable container with a medicine having a plunger, the said plunger being displaced only linearly by an integrated driving unit, suitable for immobilizing, driving, leading linearly and blocking rotation of the plunger, driven via a double action clutch, by a tensioning spring situated in the body housing, the spring tensioned by a rotary hand-dose-setting ring via the double action clutch, wherein the driving unit is activated by a trigger unit and a dose is indicated by an indicating arrangement. The automatic applicator further includes at least one block key placed in an upper part of a ratchet barrel, collaborating with at least one key placed in an internal part of the body housing.

18 Claims, 6 Drawing Sheets

Related U.S. Application Data continuation of application No. 13/459,147, filed on Apr. 28, 2012, now Pat. No. 9,566,386, which is a continuation of application No. PCT/EP2010/054128, filed on Mar. 29, 2010.

(51) Int. Cl.
*A61M 5/24* (2006.01)
*A61M 5/31* (2006.01)

(52) U.S. Cl.
CPC .... *A61M 5/31535* (2013.01); *A61M 5/31551* (2013.01); *A61M 5/31553* (2013.01); *A61M 5/31555* (2013.01); *A61M 5/31583* (2013.01); *A61M 2005/202* (2013.01); *A61M 2005/2407* (2013.01); *A61M 2005/2488* (2013.01); *A61M 2005/3115* (2013.01)

(56) References Cited

U.S. PATENT DOCUMENTS

| | | | |
|---|---|---|---|
| 5,503,627 A | 4/1996 | McKinnon et al. | |
| 5,626,566 A | 5/1997 | Petersen et al. | |
| 5,674,204 A | 10/1997 | Chanoch | |
| 6,004,297 A | 12/1999 | Steenfeldt-Jensen et al. | |
| 6,048,336 A | 4/2000 | Gabriel | |
| 6,235,004 B1 | 5/2001 | Steenfeldt-Jensen et al. | |
| 6,936,032 B1 | 8/2005 | Bush, Jr. et al. | |
| 2002/0120235 A1 | 8/2002 | Enggaard | |
| 2005/0137534 A1 | 6/2005 | Hommann | |
| 2005/0197625 A1 | 9/2005 | Haueter et al. | |
| 2005/0261634 A1 | 11/2005 | Karlsson | |
| 2006/0258988 A1 | 11/2006 | Keitel et al. | |
| 2007/0088288 A1 | 4/2007 | Barron et al. | |
| 2007/0129687 A1 | 6/2007 | Marshall et al. | |
| 2007/0244436 A1 | 10/2007 | Saiki | |
| 2008/0306445 A1 | 12/2008 | Burren et al. | |
| 2009/0054839 A1 | 2/2009 | Moller et al. | |
| 2009/0054851 A1 | 2/2009 | Radmer et al. | |
| 2009/0254047 A1 | 10/2009 | Thogersen et al. | |
| 2009/0275914 A1 | 11/2009 | Harms et al. | |
| 2009/0299297 A1 | 12/2009 | Moller et al. | |
| 2011/0224622 A1 | 9/2011 | Karlsson | |
| 2012/0197207 A1 | 8/2012 | Stefanski | |
| 2015/0045737 A1 | 2/2015 | Stefanski | |
| 2016/0101236 A1 | 4/2016 | Stefanski | |
| 2016/0101237 A1 | 4/2016 | Stefanski | |
| 2018/0008777 A1 | 1/2018 | Stefanski | |

FOREIGN PATENT DOCUMENTS

| | | | |
|---|---|---|---|
| CN | 1678362 A | 10/2005 | |
| CN | 101035580 A | 9/2007 | |
| CN | 101039712 A | 9/2007 | |
| CN | 101115520 A | 1/2008 | |
| CN | 101262899 A | 9/2008 | |
| EP | 0327910 A2 | 8/1989 | |
| EP | 0338806 A1 | 10/1989 | |
| EP | 0450905 A1 | 10/1991 | |
| EP | 0554996 A1 | 8/1993 | |
| EP | 0897728 A1 | 2/1999 | |
| JP | 63-501271 A | 5/1988 | |
| JP | 02-71758 A | 3/1990 | |
| JP | 2008-517233 A | 5/2008 | |
| JP | 2008-529690 A | 8/2008 | |
| JP | 2008-541932 A | 11/2008 | |
| JP | 2009-517157 A | 4/2009 | |
| PL | 341395 A1 | 4/2001 | |
| PL | 191327 B1 | 4/2006 | |
| PL | 211266 B1 | 4/2012 | |
| PL | 214934 B1 | 9/2013 | |
| PL | 214935 B1 | 9/2013 | |
| WO | WO 1989/007463 A1 | 8/1989 | |
| WO | WO 92/19297 A1 | 11/1992 | |
| WO | WO 1998/039041 A1 | 9/1998 | |
| WO | WO 99/38554 A1 | 8/1999 | |
| WO | WO 2001/030425 A1 | 5/2001 | |
| WO | WO 2001/072361 A1 | 10/2001 | |
| WO | WO 2001/095959 A1 | 12/2001 | |
| WO | WO 2004/024218 A1 | 3/2004 | |
| WO | WO 2005/046770 A1 | 5/2005 | |
| WO | WO 2006/045528 A1 | 5/2006 | |
| WO | WO 2006/126902 A1 | 11/2006 | |
| WO | WO 2006/130100 A1 | 12/2006 | |
| WO | WO 2009/039851 A1 | 4/2009 | |
| WO | WO 2010/089417 A2 | 8/2010 | |

AUTOMATIC APPLICATOR FOR LIQUID PHARMACEUTICAL PREPARATIONS, PARTICULARLY FOR INSULIN

CROSS-REFERENCE TO RELATED APPLICATIONS

This application is a continuation of U.S. patent application Ser. No. 15/388,385 filed on Dec. 22, 2016, which is a continuation of U.S. patent application Ser. No. 13/459,147 filed on Apr. 28, 2012 (issued as U.S. Pat. No. 9,566,386), which is a continuation of International Application No. PCT/EP2010/054128, filed on Mar. 29, 2010, which claims the benefit of P.389427, filed on Oct. 30, 2009. The disclosures of the above applications are incorporated herein by reference.

FIELD

The present disclosure concerns an automatic applicator for liquid pharmaceutical preparations, particularly for insulin, more particularly for multiple injection application of set doses of a medicine from an exchangeable container, for example for the self-application of insulin by diabetes patients.

BACKGROUND

The European patent EP 0338 806 (Holman and Marshall) teaches a syringe comprising a body, a dose-setting device in the form of a rotary cap or ring mounted on the body and capable of being moved to a selected set position where a latch is arranged to retain the setting device in that set position, the movement of the setting device being accompanied by straining of a spring, which, when the latch is released, provides the force for expelling the set dose, characterized by means arranged to release the latch, which causes the return of the setting device to an original position to drive a plunger through a one-way clutch to expel the set dose; and by a quick pitch screw thread arrangement capable of transforming rotation of the setting device into linear movement of the plunger.

Also Polish patent application P 341 395 teaches a syringe for distribution of set doses of a medicine from a cartridge containing the amount of the medicine sufficient to prepare several treatment doses, comprising a housing, a piston rod having noncircular cross-section and an external screw thread, a piston rod drive arrangement comprising two elements, i.e. piston rod leaders and a nut with an internal screw thread corresponding to the piston rod external screw thread, as well as a dose-setting mechanism comprising non-self-blocking screw thread connection, along which an injection push-button is unscrewed from the nearer housing end, causing rotation of the dose-setting element. This syringe is characterized in that between the nut and the piston rod leaders there is unidirectional coupling enabling the rotation of both these parts in one direction but not in the opposite direction, wherein the allowed rotation is the only one, by means of which the piston rod is moved in the circumferential direction in the syringe. The coupling is designed in such way that the initial resistance, sufficient to resist the torque exerted on the coupling by setting a dose, has to be overcome to allow rotation. The marks indicating the size of the selected dose could be placed under the housing.

The main disadvantage of the known devices is lack of the provision of application of the precisely controlled and set dose of a medicine.

The above discussed syringe for manual application of a medicine requires from a patient the manual adjustment of the pressure force on the injection push-button, which defines the speed of the injection. This causes additional stress and discomfort at application. An additional disadvantage is a complex arrangement to transform the linear displacement of the injection pushbutton into the linear displacement of the piston rod by means of the rotary movement of the nut. Other disadvantages of a syringe for an application of a medicine using a tensioned spring comprise the failure prone construction of the trigger device, which does not ensure reliable nut blocking, and the lack of an external guiding means for the tensioned spring. This negatively affects maintaining the control and the precision of the application of the set dose of a medicine.

Besides, known devices do not ensure adequate protection against damaging the clutch or the driving arrangement due to excessive rotation of the dose-setting element. Also, forces of friction opposing the action of the plunger are too large. The arrangements for dose indication in known devices are too complex and the scale usually placed on the external surface of the housing can be easily effaced.

SUMMARY

One aim of the present disclosure concerning an automatic applicator particularly for insulin, more particularly for multiple injection application of set doses of a medicine from an exchangeable container, is to ensure a capability for the precisely controlled application of the set dose of a medicine, preserving an automatic application of the medicine without any stress, providing external guidance for the tensioned spring and providing adequate protection against damaging the clutch or the driving arrangement due to excessive rotation of the dose-setting element.

Another aim of the present disclosure is to ensure the reduction of forces of friction opposing the action of the plunger and provide reliable nut blocking by means of a reliable construction of a trigger device, preserving an automatic application of the medicine.

Yet another aim of the present invention concerning an automatic applicator is to ensure an indicator device having the scale marks placed not on the external surface of the housing, which prevents effacing them during the operating of the applicator by its user.

An automatic applicator for liquid pharmaceutical preparations is provided, particularly for insulin, more particularly for multiple injection application of set doses of a medicine from an exchangeable container, comprising a body housing connected to a housing of an exchangeable container with a medicine, particularly insulin, having a plunger, suitable for expelling the medicine, a plunger being displaced linearly by an integrated driving unit, suitable for immobilizing, driving, leading linearly and blocking rotation of the plunger, driven via a double action clutch, by a tensioning spring situated in the body housing, the spring tensioned by a rotary hand-dose-setting ring via the same double action clutch unit, wherein the driving unit is activated by a trigger unit and a dose is indicated by an indicating arrangement. According to the present disclosure the automatic applicator comprises at least one block key placed in the upper part of the ratchet barrel, collaborating with at least one key placed in the internal part of the cylindrical body housing.

The novel construction of the automatic applicator enables the precisely controlled application of the set dose of a medicine, preserving an automatic application of the medicine without any stress, providing external guidance for the tensioned spring and providing adequate protection against damaging the clutch or the driving arrangement due to excessive rotation of the dose-setting element.

Advantageously the automatic applicator comprises two block keys placed directly on the circumferential surface of the ratchet barrel, collaborating with two keys on the internal part of the cylindrical surface of the cylindrical body housing, placed above a viewing window.

An automatic applicator variant is provided wherein the integrated driving unit, suitable for immobilizing, driving, leading linearly and blocking rotation of the plunger, comprises a plunger block guide and a driving nut, whereas the plunger block guide is blocked in a toothed ring of the seat element, urged to it by means of the container housing of the exchangeable insulin container, and in the said integrated driving unit a nut is bearingly mounted in a seat element, advantageously by means of a ball bearing.

Owing to such construction, there is provided reliable driving nut blocking, minimally affecting the positioning of the nut and simultaneously preventing any its rotation or influencing the position of the plunger during dose setting, as well as ensured the reduction of forces of friction opposing the action of the plunger.

Further, advantageously the driving tensioning spring is a twisted spring and the second spring is placed directly under the trigger unit.

A further automatic applicator variant is provided, in which the indicating arrangement comprises a scale deposited linearly on a cylindrical part of the ratchet barrel under the block keys and a inspection window situated in the housing. Owing to such construction, the scale is appropriately displaced during dose setting and is well visible in the inspection window.

DRAWINGS

In order that the disclosure may be well understood, there will now be described various forms thereof, given by way of example, reference being made to the accompanying drawings, in which.

DETAILED DESCRIPTION

The following description is merely exemplary in nature and is not intended to limit the present disclosure, application, or uses.

Figure 1:
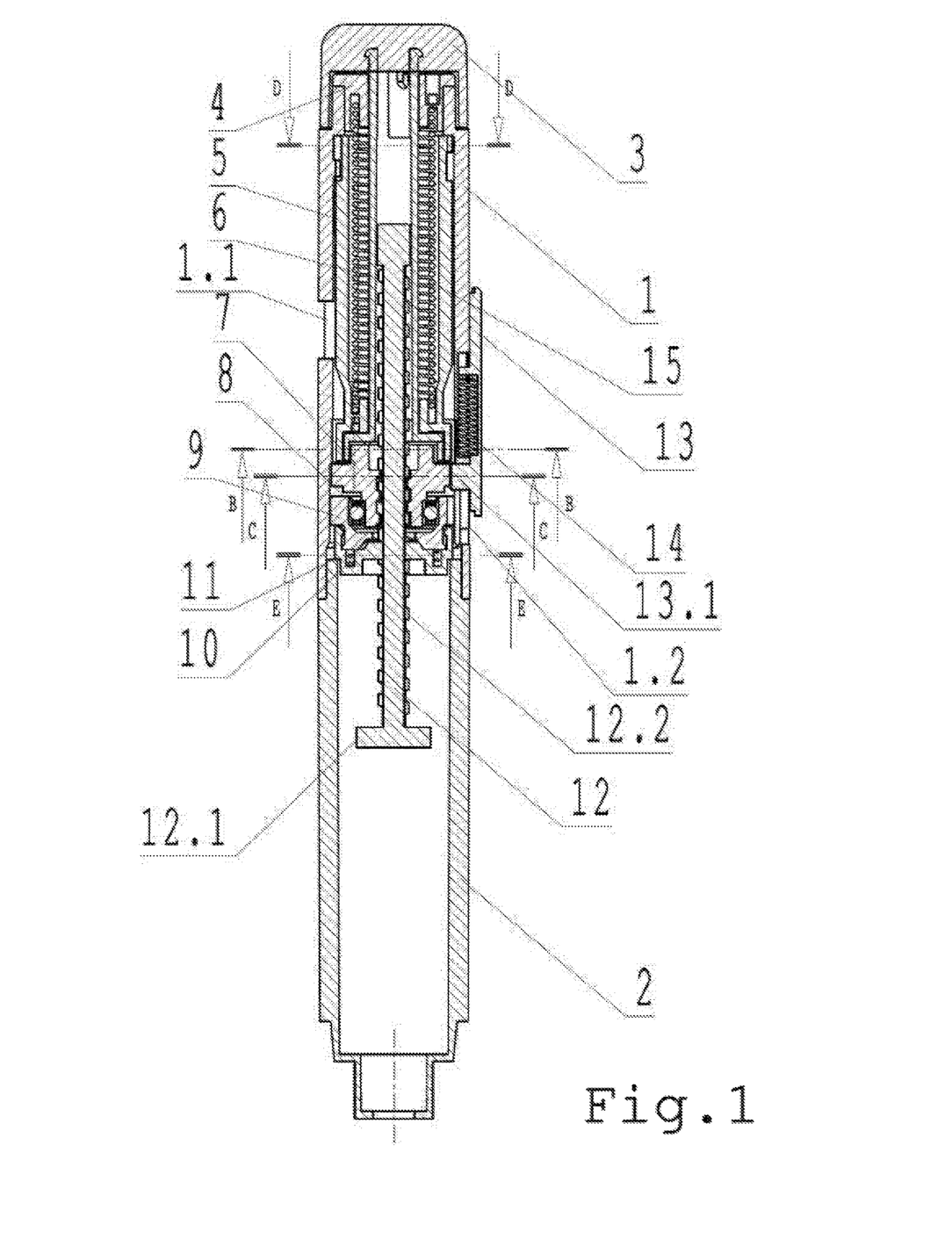
FIG. 1 presents the longitudinal section of the automatic applicator, without an exchangeable container and its casing.
Figure 6:
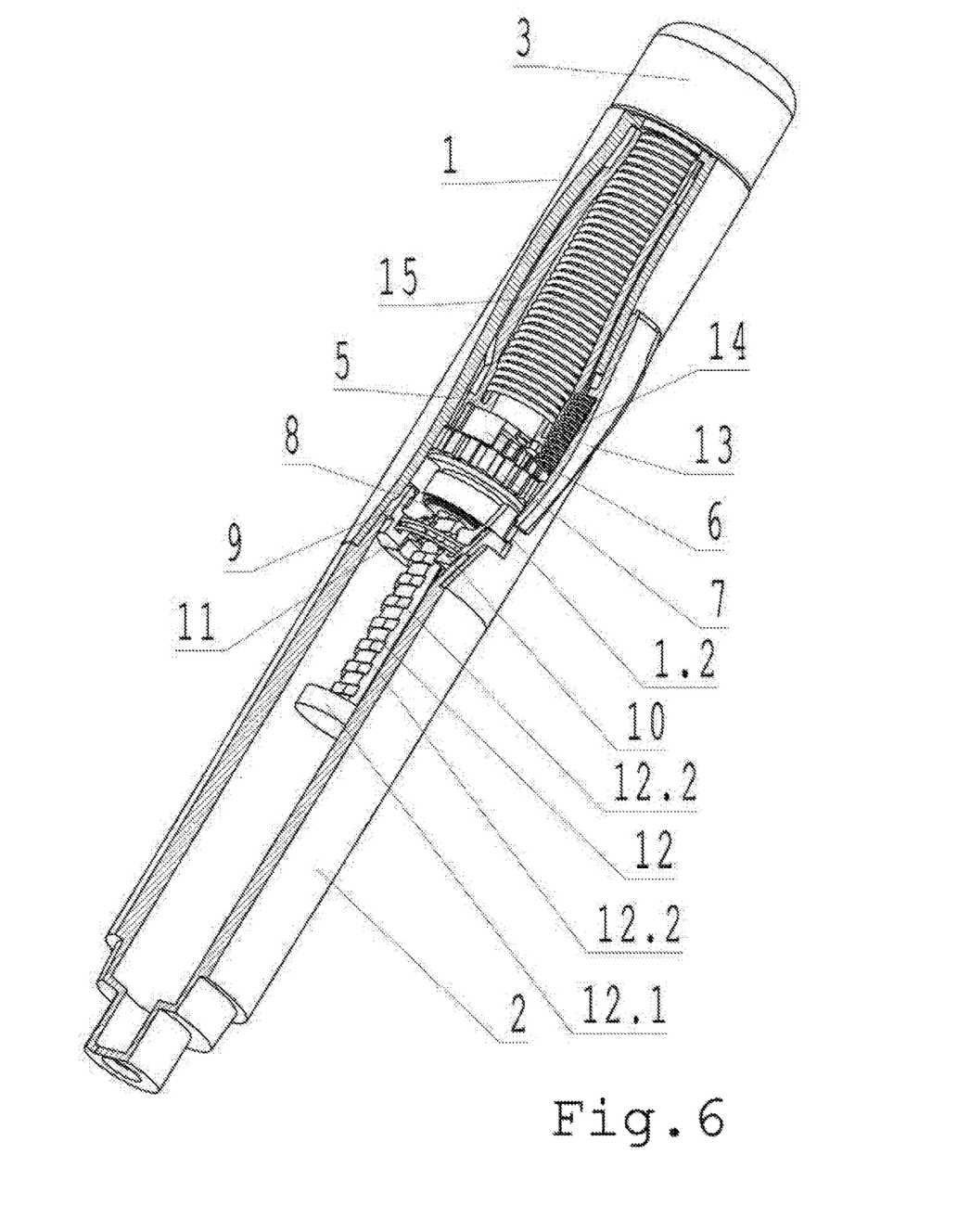
FIG. 6 presents the front axonometric view of the automatic applicator from the FIG. 1, with parts of the housings removed, showing the advantageous mutual positioning of the elements of the internal mechanisms of the automatic applicator.
Figure 7:
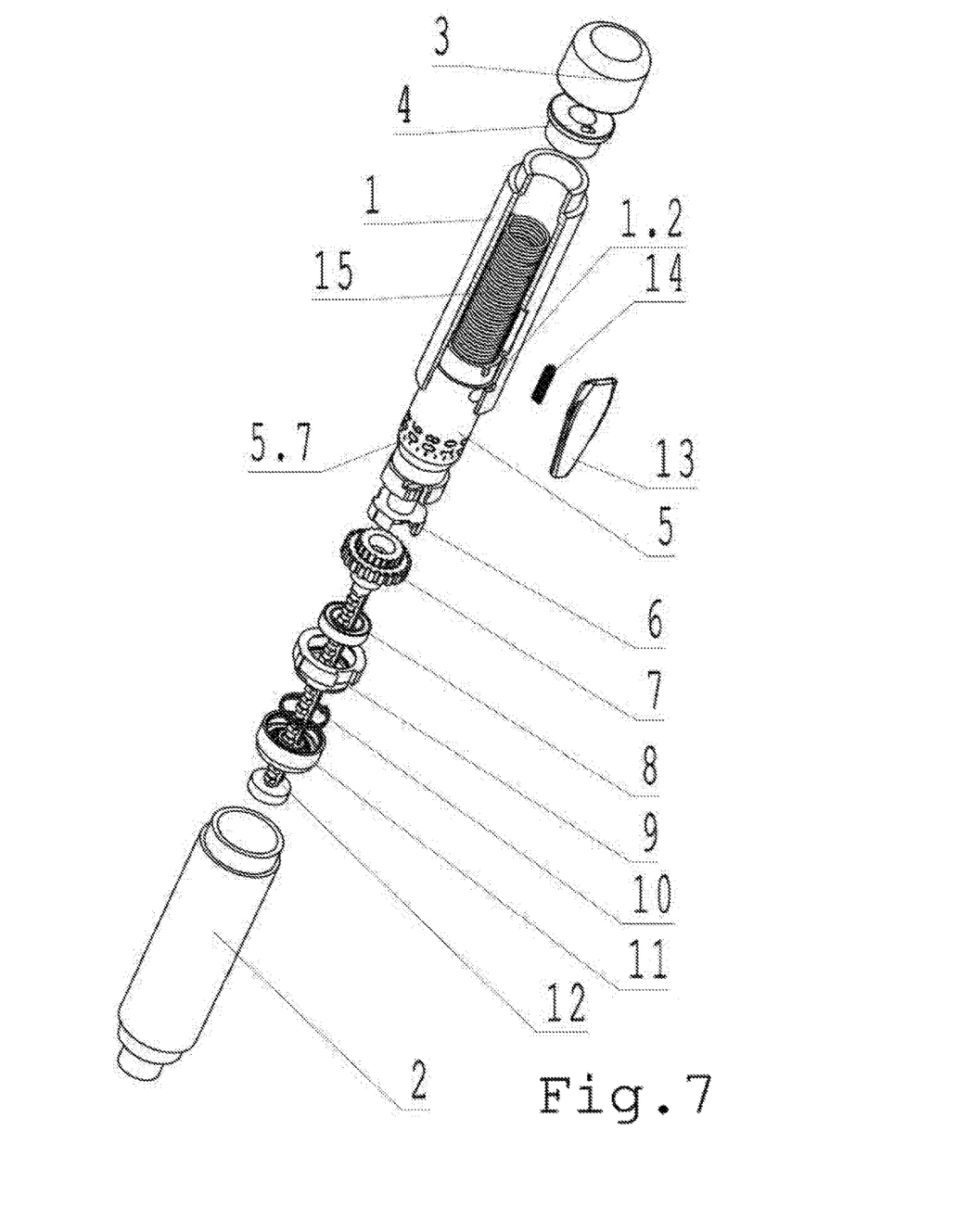
FIG. 7 presents the exploded front axonometric view of the automatic applicator from the FIG. 1.

As shown in the FIGS. 1, 6 and 7, an automatic applicator for liquid pharmaceutical preparations, particularly for insulin, more particularly for multiple injection application of set doses of a medicine from an exchangeable container, comprises the body housing 1, connected to the housing 2 of the exchangeable container with a medicine (not shown in the drawings). The insulin is expelled by the plunger 12, linearly displaced by means of the driving unit, suitable for immobilizing, driving, leading linearly and blocking rotation of the plunger 12, driven via a double clutch unit by the tensioning spring 15, wherein the driving tensioning spring 15 is a twisted spring situated in the body housing 1, tensioned by the rotary hand-dose-setting ring 3 also via a double clutch unit, wherein the driving unit is activated by the trigger unit and the displaceable indicating cylinder 14 is situated on the tensioning spring holder 13 and a scale 5.7 with the scale visible in the inspection window 1.1 deposited on the ratchet barrel 5.

The automatic applicator for liquid pharmaceutical preparations, particularly for insulin, more particularly for multiple injection application of set doses of a medicine from an exchangeable container, operates as follows.

In order to replace the insulin container you should unscrew the container housing 2, which is connected to the body housing 1 (FIG. 1) by turning it anticlockwise. After unscrewing the container housing 2, the plunger block guide 11 and the seat element 9 become automatically disengaged owing to the action of the disengaging spring 10 by means of moving the plunger block guide 11 coaxially in the direction of plunger 12. This enables hand backing of the plunger 12 by using the force in the axial direction to push it into the housing 1. The plunger ending 12.1 is independently rotated on the plunger 12. The coupling between the plunger 12 and the nut 7 is by a quick thread, so while being pushed into the housing 1 the plunger 12 screws itself into the nut 7. The plunger should be pushed until it almost completely hides in the housing 1, which allows a new container with insulin to be inserted.

The nut 7 is coupled to the plunger 12 by a thread having pitch enabling application of the appropriate dose of insulin. Further, the nut is bearingly mounted in the seat element 9, advantageously by means of a ball bearing 8.

Then you should remove the needle (not shown) mounted on the container housing 2 by turning it anti-clockwise, remove the empty container by withdrawing it from the housing 2 and install a new container.

To install a new container you should insert it into the container housing 2, which you should place in the body housing 1 by turning it clockwise. Next you should fix a new needle and cover it with the protecting cap.

The dose-setting is carried out by turning the rotary hand-dose-setting ring 3 (FIG. 1) clockwise. The currently set dose can be seen on the cylindrical part of the ratchet barrel 5 by means of the inspection window 1.1 situated in the housing 1, which together with the scale 5.7 deposited linearly on a under the block keys 5.6 comprises the indicating arrangement. The cylinder of the ratchet barrel 5 is scaled by every four units and the turning of the rotary hand-dose setting ring 3 is accompanied by a characteristic clicking at every two units, corresponding to 0.02 ml of insulin. The dose-setting can be realized up to two units, wherein the scale 5.7 visible through the inspection window 1.1, stops at any value or between the given dose values, which is easy to check as two consecutive doses are then seen in inspection window 1.1, and a red line indicator shows the position between them.

The rotary hand-dose-setting ring 3 is rigidly connected to the coupling sleeve 6. When a dose is to be increased, the coupling sleeve 6 (FIG. 2) is rotated clockwise (looking in the direction of the needle) wherein the resilient arm of the pawl 5.3 is displaced on the slide edges 7.5 of the ratchet tooth ring 7.1 of the stationary driving nut 7, from one blocking edge of the ratchet tooth ring 7.1 to the neighbour edge(s) depending on the angle of rotation. The ratchet barrel 5 is driven by the coupling sleeve 6 by means of the steering recess 6.1 made in the inner wall of the coupling sleeve 6 meshed with the key 5.4 situated in the inner wall of the ratchet barrel 5. Therefore, when the coupling sleeve 6 is rotated, the ratchet barrel 5 is rotated together with it. During the rotation in the clockwise direction, the resilient arm of the pawl 5.3 is displaced radially, alternatively inside and outside.

Figure 2:
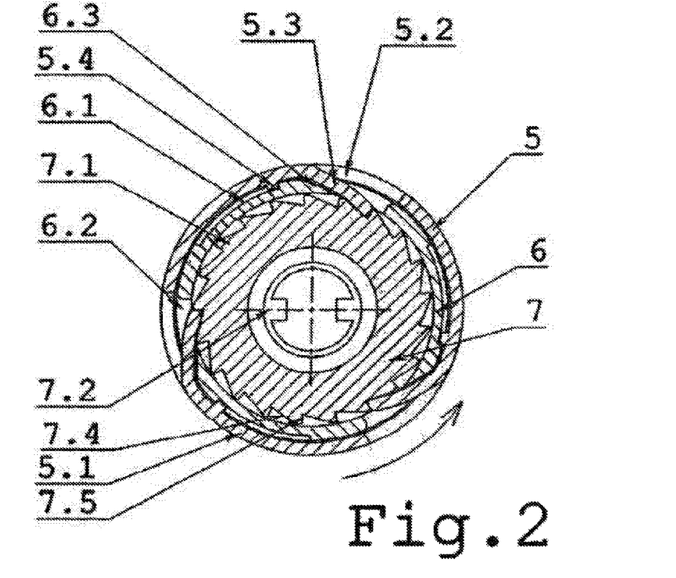
FIG. 2 presents the cross-section B-B of the ratchet mechanism of the automatic applicator with the pawls meshed with the toothed ring of the nut.

The ratchet barrel 5 is rigidly connected to the spring 15, which in turn is connected to spring block 4. The spring block 4 is rigidly connected to the housing 1 and secured against rotation.

Figure 3:
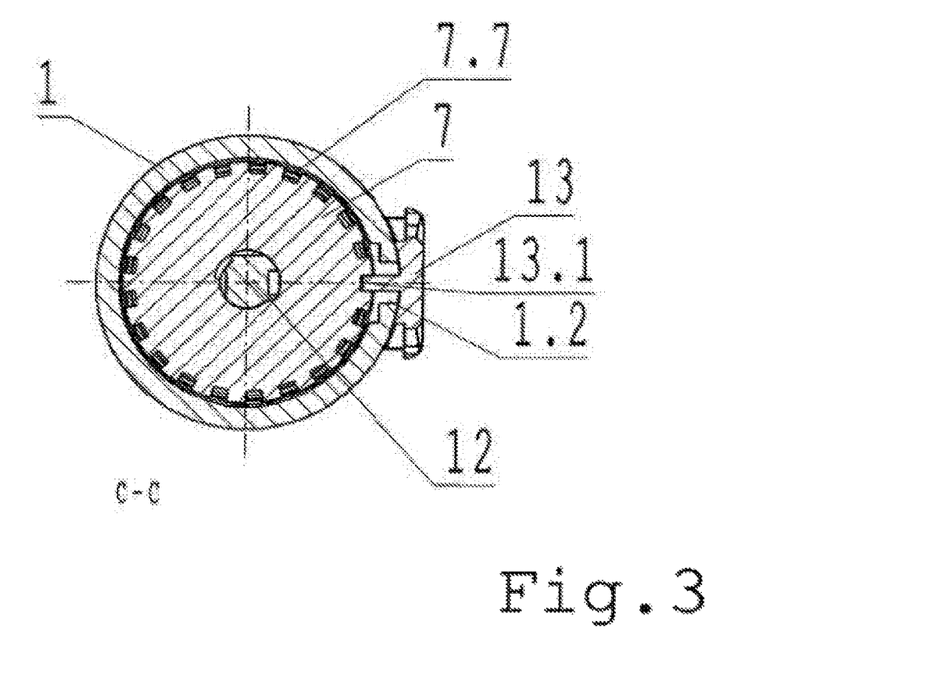
FIG. 3 presents the cross-section C-C of the automatic applicator from the FIG. 1, in the place, in which the trigger mechanism meshes with the toothed ring of the nut.

During the dose setting the nut 7 is immobilized by the trigger unit 13 by means of the rectangular grooves 7.7 (FIG. 3) situated on the circumference of the nut 7, collaborating with the key 13.1 of the trigger unit 13.

Figure 4:
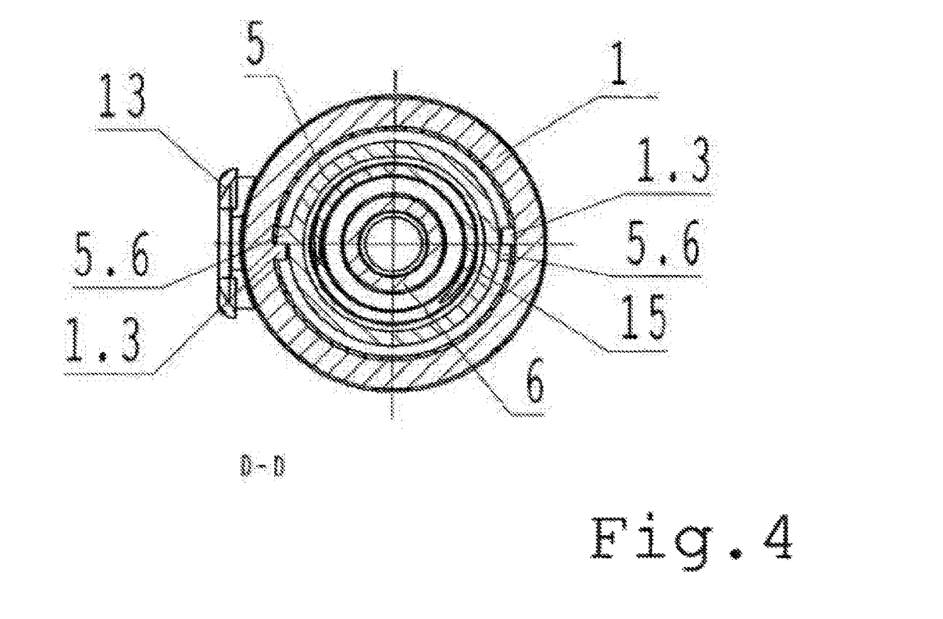
FIG. 4 presents the cross-section O-O of the automatic applicator from the FIG. 1, showing the system blocking the rotation of the scale, which defines the working range of the automatic applicator.

The operational range of the automatic applicator is defined by two block keys 5.6 (FIG. 4) placed directly on the circumferential surface of the ratchet barrel 5, collaborating with two keys 1.3 on the internal part of the cylindrical surface of the cylindrical housing 1 placed above the inspection window 1.1. The keys are situated on the opposite sides and simultaneously slightly displaced axially. Such arrangement enables realizing one incomplete rotation of the dose setting elements.

Figure 5:
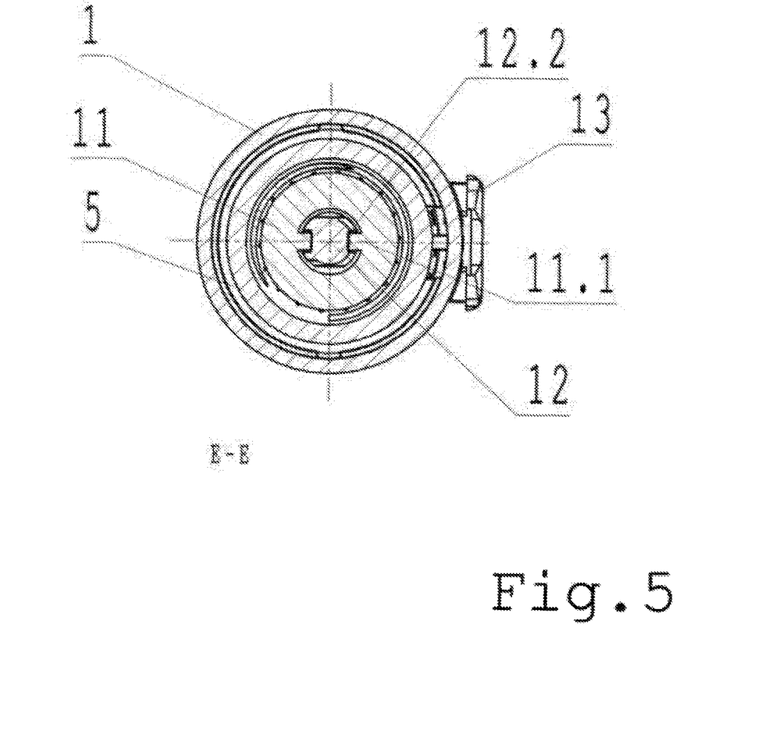
FIG. 5 presents pictorially the cross-section E-E of the automatic applicator from the FIG. 1, showing the positioning of the elements of the arrangement blocking the plunger against rotation.

After setting the dose you can actuate the dosing of insulin by pressing the trigger unit 13 in the direction of the needle. The trigger unit 13 should be pressed throughout the whole time of the insulin application. The range of the trigger displacement is defined by the displacement of the key 13.1 in the corresponding groove 1.2 in the body housing 1. After pressing the trigger unit 13 the nut 7 is released by the disengagement of the ring with the rectangular grooves 7.7 and the key 13.1 of the trigger unit 13. The mechanism starts rotating, driven by the force from the tensioning spring 15. The nut 7 causes the unscrewing of the plunger 12 on the thread 12.1 of the plunger 12. The rotation of the plunger is blocked by the key 11.1 of the plunger block guide 11 and the recess 12.2 made in the plunger 12 (FIG. 5). The plunger 12 acts directly on the piston of the insulin container, placed in the container housing 2. It causes the injection of insulin from the needle mounted on the container housing 2. This action is accompanied by the reverse movement of the whole mechanism to its initial position, i.e. the tensioning spring 15 unwinds, and the ratchet barrel 5 with the scale 5.7 returns to the position "0".

After completing the dose-setting you can release the trigger unit 13. The trigger unit 13 will then automatically return to its initial position urged by the spring 14, which is placed directly under the trigger unit 13, and will again block the nut 7.

The double action clutch, best seen in the FIG. 2, which presents the cross-section B-B of the ratchet mechanism of the automatic applicator with the pawls meshed with the toothed ring of the nut, comprises the coupling sleeve 6 radially coupled with the body of the ratchet barrel 5 and coupled with the pawls 5.3 having hooks separately meshed with the gear ring 7.5 of the driving nut 7.

The coupling sleeve 6 is rigidly connected to the rotary hand-dose-setting ring 3 and the body of the ratchet barrel 5 is rigidly connected to the tensioning spring 15 holder, in the form of a protective sleeve, which enables transfer of the rotation of the rotary hand-dose-setting ring 3 to the tensioning spring 15 holder.

The tensioning spring 15 (FIG. 1 and FIG. 6) is mounted, form the side of the needle, in the tensioning spring 15 holder, in the form of a protective sleeve rigidly connected to the body of the ratchet barrel 5.

The integrated driving unit (FIG. 5), suitable for immobilizing, driving, leading linearly and blocking rotation of the plunger 12 comprises a plunger block guide 11 and a driving nut 7. The construction of the integrated driving unit enables hand backing of the plunger 12 by pushing it into the driving nut 7 in such way that it minimally protrudes from the housing, allows a new container, ego with insulin, to be inserted.

The nut 7 (as mentioned above) is coupled to the plunger 12 by a thread having pitch enabling application of the appropriate dose of insulin. Additionally, the plunger 12 comprises at least one longitudinal groove enabling linear displacement of the plunger 12 in the plunger block guide 11 by means of at least one key.

The trigger unit (FIG. 3) constitutes the trigger 13 with the key 13.1 slidingly displaced in the groove 1.2 situated in the housing 1 in order to block the ring with the rectangular grooves 7.7 of the driving nut 7.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

The invention claimed is:
1. A multiple injection application device comprising:
a housing and at least two springs,
wherein a first spring of the at least two springs is positioned inside the housing,
wherein the first spring is a driving helical spring,
wherein the housing comprises a wall, an inspection window, an open distal end and an open proximal end,
wherein the open distal end of the housing comprises an external diameter and the open proximal end of the housing comprises an external diameter, the external diameter of the open proximal end of the housing being smaller than the external diameter of the open distal end of the housing,
a spring block connected to the open proximal end of the housing and secured against rotation relative to the housing,
wherein the spring block comprises a distal end and a proximal end, the proximal end of the spring block being wider than the distal end the spring block,
wherein the proximal end of the spring block at least partially covers the wall of the housing, wherein the driving helical spring is connected to the spring block and a rotary dose knob is adapted to twist the driving helical spring relative to the housing via a coupling sleeve, wherein the rotary dose knob is substantially axially immovable relative to the housing and comprises a cavity, wherein the spring block comprises a first hole and a second hole, the first hole of the spring block being separated from the second hole of the spring block by a wall of the spring block, the first hole of the spring block comprising a longitudinal axis that is parallel to a longitudinal axis of the second hole of the spring block, the first hole of the spring block comprising an internal diameter, the second hole of the spring block comprising an internal diameter;

wherein the coupling sleeve extends through the first hole of the spring block and is arranged non-coaxially with the second hole of the spring block, the coupling sleeve comprising an outer diameter that is smaller than the internal diameter of the first hole of the spring block and is larger than the internal diameter of the second hole of the spring block, wherein the cavity of the rotary dose knob at least partially surrounds the wall of the housing, the spring block, the driving helical spring, and the coupling sleeve, wherein the coupling sleeve is at least partially surrounded by the wall of the spring block that separates the first hole of the spring block from the second hole of the spring block, wherein the coupling sleeve comprises a substantially cylindrical portion and the coupling sleeve extends above the housing, wherein a plunger suitable for expelling a medicine is at least partially covered by the coupling sleeve, wherein the plunger comprises a thread, a first longitudinal groove and a second longitudinal groove, the plunger comprising a longitudinal direction, the first longitudinal groove of the plunger and the second longitudinal groove of the plunger each extending through at least a portion of the thread of the plunger in the longitudinal direction of the plunger, wherein the first longitudinal groove of the plunger and the second longitudinal groove of the plunger are positioned opposite one another, and wherein the rotary dose knob, the spring block, the coupling sleeve extending through the first hole, the plunger, and the driving helical spring are arranged coaxially.

2. The multiple injection application device according to claim 1, wherein the coupling sleeve comprises a clutch element.

3. The multiple injection application device according to claim 2, wherein the clutch element comprises a curved portion.

4. The multiple injection application device according to claim 1, wherein the at least two springs comprise a second spring which is a helical spring.

5. The multiple injection application device according claim 1, wherein the rotary dose knob is coupled to the coupling sleeve such that when a dose is to be increased, the coupling sleeve rotates clockwise relative to the housing.

6. The multiple injection application device according claim 1, wherein when the coupling sleeve is rotated by turning the rotary dose knob for increasing a dose, a resilient arm of a pawl is displaced radially.

7. The multiple injection application device according claim 1, wherein the first longitudinal groove of the plunger is adapted to receive a first key and the second longitudinal groove is adapted to receive a second key.

8. The multiple injection application device according to claim 7, wherein the first key is rotationally blocked in relation to the plunger.

9. The multiple injection application device according to claim 7, wherein the first key and the second key are portions of a plunger guide, the plunger guide being located within an interior of the housing.

10. The multiple injection application device according claim 9, wherein the plunger guide is axially movable relative to the housing.

11. The multiple injection application device according to claim 1, wherein
the at least two springs comprise a second spring, and
the second spring is at least partially outside the housing.

12. The multiple injection application device according to claim 1, wherein the at least two springs comprise a second spring that comprises at least one coil.

13. The multiple injection application device according to claim 1, wherein
the housing comprises an internal diameter,
the proximal end of the spring block comprises an external diameter, and
the external diameter of at least a portion of the proximal end of the spring block is greater than the internal diameter of the housing.

14. The multiple injection application device according to claim 1, wherein the plunger comprises a proximal non-threaded end and a distal threaded portion.

15. The multiple injection application device according to claim 14, wherein at least a portion of the proximal non-threaded end of the plunger is wider than the distal threaded portion of the plunger.

16. The multiple injection application device according to claim 1, wherein the coupling sleeve comprises at least a first protrusion and a second protrusion.

17. The multiple injection application device according to claim 16, wherein at least a portion of the first protrusion of the coupling sleeve is above the driving helical spring.

18. The multiple injection application device according to claim 16, wherein at least a portion of the second protrusion of the coupling sleeve is below the driving helical spring.

* * * * *